(12) United States Patent
Peng et al.

(10) Patent No.: US 11,172,822 B2
(45) Date of Patent: Nov. 16, 2021

(54) SYSTEM AND METHOD FOR ANALYZING BRAIN TISSUE COMPONENTS BASED ON MAGNETIC RESONANCE IMAGE

(71) Applicants: TAIPEI VETERANS GENERAL HOSPITAL, Taipei (TW); NATIONAL CHIAO TUNG UNIVERSITY, Hsinchu (TW)

(72) Inventors: Syu-Jyun Peng, Hsinchu County (TW); Cheng-Chia Lee, Taipei (TW); Huai-Che Yang, Taipei (TW)

(73) Assignees: TAIPEI VETERANS GENERAL HOSPITAL, Taipei (TW); NATIONAL CHIAO TUNG UNIVERSITY, Hsinchu (TW)

( * ) Notice: Subject to any disclaimer, the term of this patent is extended or adjusted under 35 U.S.C. 154(b) by 69 days.

(21) Appl. No.: 16/553,160

(22) Filed: Aug. 27, 2019

(65) Prior Publication Data
US 2020/0397293 A1   Dec. 24, 2020

(30) Foreign Application Priority Data
Jun. 20, 2019   (TW) .................................. 108121561

(51) Int. Cl.
| A61B 5/00 | (2006.01) |
| A61B 5/055 | (2006.01) |
| G06T 7/143 | (2017.01) |
| G06T 7/11 | (2017.01) |

(52) U.S. Cl.
CPC ............ *A61B 5/0042* (2013.01); *A61B 5/055* (2013.01); *A61B 5/4064* (2013.01); *G06T 7/11* (2017.01); *G06T 7/143* (2017.01)

(58) Field of Classification Search
CPC ....... A61B 5/0042; A61B 5/055; G06T 7/143; G06T 7/11
See application file for complete search history.

(56) References Cited

U.S. PATENT DOCUMENTS

| 9,870,614 B1 | 1/2018 | Chou et al. |
| 10,346,719 B2 * | 7/2019 | Peng ...................... A61B 5/055 |
| 10,779,762 B2 * | 9/2020 | Yablonskiy .......... A61B 5/0042 |

(Continued)

FOREIGN PATENT DOCUMENTS

| CN | 103826536 B | 11/2016 |
| CN | 106651874 A | 5/2017 |

(Continued)

*Primary Examiner* — Khai M Nguyen
(74) *Attorney, Agent, or Firm* — CKC & Partners Co., LLC

(57) ABSTRACT

A system for analyzing brain tissue components based on magnetic resonance image. The system includes a memory and a processor. The memory stores instructions. The processor accesses and executes the instructions to perform the following: extracting maps of tissue from a brain magnetic resonance imaging (MRI) corresponding to normal subjects; averaging the maps of tissue according to a number of the normal subjects to generate reference maps that correspond to different tissues; receiving a brain MRI sample having a targeted region; and analyzing the brain MRI sample based on the reference maps and the targeted region to generate an analysis result, in which the analysis result indicates a ratio of tissues in the targeted region of the brain MRI sample.

10 Claims, 6 Drawing Sheets

(56) References Cited

U.S. PATENT DOCUMENTS

| | | | | |
|---|---|---|---|---|
| 2010/0244834 A1* | 9/2010 | Mori | ............... | G01R 33/56341 |
| | | | | 324/310 |
| 2011/0033099 A1* | 2/2011 | Kadomura | ............. | A61B 6/032 |
| | | | | 382/131 |
| 2011/0044524 A1* | 2/2011 | Wang | ..................... | G01R 33/54 |
| | | | | 382/131 |
| 2013/0317341 A1* | 11/2013 | Spies | .................. | G06T 7/0014 |
| | | | | 600/410 |
| 2014/0307936 A1* | 10/2014 | Dore | .................... | G06T 7/0016 |
| | | | | 382/131 |
| 2015/0185298 A1* | 7/2015 | Crozier | ................... | G06F 17/10 |
| | | | | 702/19 |
| 2015/0221089 A1* | 8/2015 | Funabasama | ...... | A61B 5/02755 |
| | | | | 382/130 |
| 2016/0109539 A1* | 4/2016 | Mardor | ............... | A61B 5/4848 |
| | | | | 600/420 |
| 2016/0350933 A1* | 12/2016 | Schieke | ................. | G16H 30/40 |
| 2017/0140551 A1* | 5/2017 | Bauer | ................. | G06K 9/6256 |
| 2019/0029557 A1* | 1/2019 | Chen | ................. | G01R 33/4806 |
| 2021/0082113 A1* | 3/2021 | Jara | ...................... | G06T 11/008 |

FOREIGN PATENT DOCUMENTS

| | | |
|---|---|---|
| CN | 103793593 B | 2/2018 |
| EP | 1328189 B1 | 8/2016 |
| TW | 499307 B | 8/2002 |
| TW | 201143707 A | 12/2011 |
| TW | I542328 B | 7/2016 |
| TW | 201909845 A | 3/2019 |

\* cited by examiner

_US 11,172,822 B2_

SYSTEM AND METHOD FOR ANALYZING BRAIN TISSUE COMPONENTS BASED ON MAGNETIC RESONANCE IMAGE

CROSS-REFERENCE TO RELATED APPLICATION

This application claims priority to Taiwan Application Serial Number 108121561, filed on Jun. 20, 2019, which is herein incorporated by reference.

BACKGROUND

Technical Field

Present disclosure relates to an electronic system and a method. More particularly, the present disclosure relates to a system and a method for analyzing MRI with brain lesions in order to determine brain tissue distribution of the lesions.

Description of Related Art

Brain tumors can cause symptoms of epilepsy in patients, especially those supratentorial tumors spread to gray matters. Previous studies show that 50%-63% of supratentorial brain tumors can cause epilepsy symptoms. Previous studies also show that about 57%-70% of brain tumors spreading to gray matters can cause epilepsy symptoms. In the contrary, a chance for brain tumors failing to spread to gray matters to cause epilepsy symptoms is about 14-20%.

In current approaches, magnetic resonance imaging (MRI) systems can be used to scan patients' brains for diagnosis. However, an accurate ratio of the tissue distribution in the MRI can be hard to find since tumors can destroy some brain tissues. Therefore, current MRI systems are often failed to obtain effective analysis results.

SUMMARY

An aspect of the present disclosure is related to a system for analyzing brain tissue components based on magnetic resonance image. The system for analyzing brain tissue components based on magnetic resonance image includes a memory and a processor. The processor is communicatively coupled to the memory. The memory stores at least one instruction. The processor is configured to access and execute the at least one instruction to perform the following: extract a plurality of tissue maps from a plurality of brain magnetic resonance imaging (MRI) corresponding to a plurality of normal subjects; average the plurality of tissue maps based on a number of the plurality of normal subjects, in order to generate a plurality of reference tissue maps, wherein the plurality of reference tissue maps are corresponding to different tissues; receive a brain MRI sample having a target area marked thereon; and analyze the brain MRI sample based on the plurality of reference tissue maps and the target area, in order to generate an analysis result, wherein the analysis result indicates a ratio of tissues corresponding to the target area of the brain MRI sample.

Another aspect of the present disclosure are related to a method for analyzing brain tissue components based on magnetic resonance image. The method for analyzing brain tissue based on magnetic resonance image includes following steps: extracting a plurality of tissue maps from a plurality of brain magnetic resonance imaging corresponding to a plurality of normal subjects; averaging the plurality of tissue maps based on a number of the plurality of normal subjects, in order to generate a plurality of reference tissue maps, wherein the plurality of reference tissue maps are corresponding to different tissues; receiving a brain MRI sample having a target area marked thereon; and analyzing the brain MRI sample based on the plurality of reference tissue maps and the target area, in order to generate an analysis result, wherein the analysis result indicates a ratio of tissues corresponding to the target area of the brain MRI sample.

It is noted that the foregoing summary and the embodiments described hereinafter are merely examples for illustrating the content of the claims of the present disclosure.

BRIEF DESCRIPTION OF THE DRAWINGS

Reference can be made to embodiments and drawings in following paragraphs for better understandings of present disclosure.

DETAILED DESCRIPTION

Figure 1:
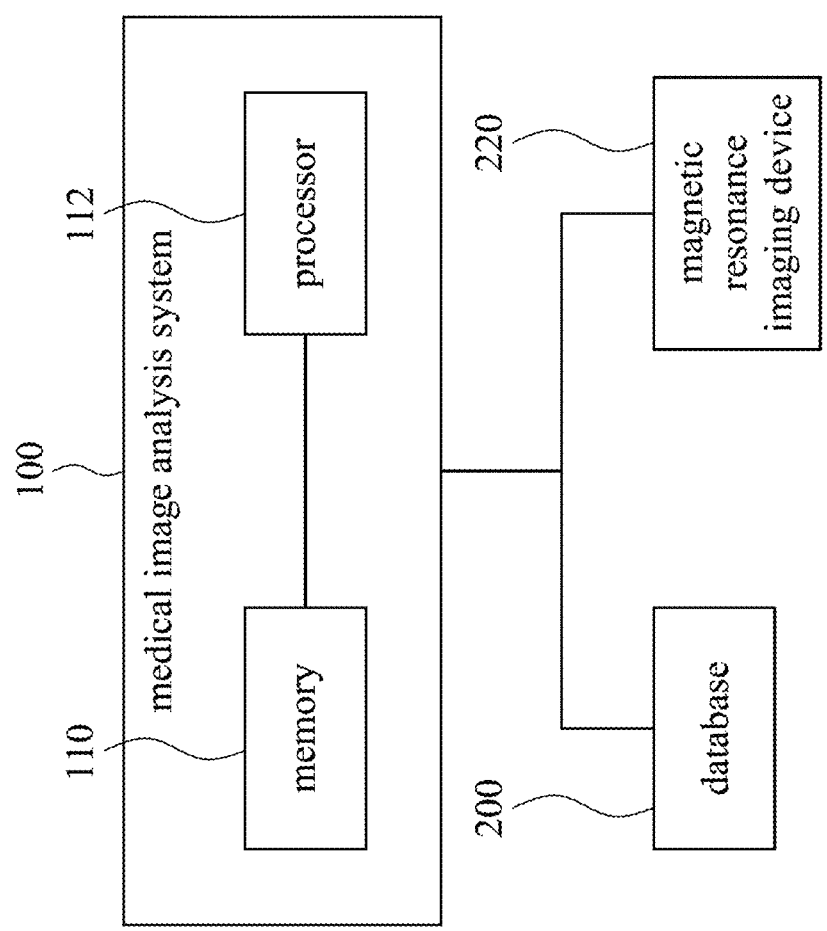
FIG. 1 is a schematic diagram showing a medical image analysis system according to some embodiments of the present disclosure.

Reference will now be made in detail to the present embodiments of the disclosure, examples of which are illustrated in the accompanying drawings. Wherever possible, the same reference numbers are used in the drawings and the description to refer to the same or like parts.

The terminology used herein is for describing particular embodiments only and is not intended to be limiting of the present disclosure. As used herein, the singular forms "a," "an," "this," and "the" are intended to include the plural forms as well, unless the context clearly indicates otherwise.

In the following description and claims, the terms "coupled" and "connected", along with their derivatives, may be used. In particular embodiments, "connected" and "coupled" may be used to indicate that two or more elements are in direct physical or electrical contact with each other, or may also mean that two or more elements may be in indirect contact with each other. "Coupled" and "connected" may still be used to indicate that two or more elements cooperate or interact with each other.

As used herein, the terms "comprising," "including," "having," and the like are to be understood to be open-ended, i.e., to mean including but not limited to.

As used herein, the term "and/or" includes any and all combinations of one or more of the associated listed items.

The terms used in this specification generally have their ordinary meanings in the art and in the specific context where each term is used. Some terms used to describe the present disclosure are discussed below or elsewhere in this specification, in order to provide additional guidance to those skilled in the art in the description of the present disclosure.

FIG. 1 is a schematic diagram showing a medical image analysis system 100 according to some embodiments of the present disclosure. As shown in FIG. 1, in some embodiments, the medical image analysis system 100 can include a memory 110 and a processor 112. In some embodiments, the medical image analysis system 100 can be an analysis system, especially a system for analyzing brain tissue components based on magnetic resonance imaging (MRI).

In some embodiments, the memory 110 can be a flash memory, a hard disk drive (HDD), a solid-state drive (SSD), a dynamic random access memory (DRAM) and a static random access memory (SRAM). In some embodiments, the memory 110 can store at least one instruction. The instruction relates to a medical image analysis method, especially a method for analyzing brain tissue based on magnetic resonance imaging.

In some embodiments, the processor 112 can include, but not limited to, a single processor or an integration of multiple microprocessors, such as a central processing unit (CPU), a graphics processing unit (GPU), etc. The processors are electrically coupled to the memory. In this way, the processor 112 can access the instruction from the memory 110 and execute specific applications based on the instruction, in order to perform mentioned medical image analysis method. For better understandings of the medical image analysis method, details of the method are introduced in following paragraphs.

As shown in FIG. 1, in some embodiments, the processor 112 can be selected to communicatively coupled to the database 200. In some embodiments, the database 200 can store a plurality of MRI, especially brain MRI corresponding to a plurality of normal subjects. In some embodiments, the database 200 can be implemented by some external servers out of the medical image analysis system 100. In some embodiments, the database 200 can be implemented by the memory 110.

As shown in FIG. 1, the processor 112 can be selected to communicatively coupled to a magnetic resonance imaging (MRI) device 220. In some embodiments, the MRI device 220 can be operational for generating MRI, especially the brain MRI corresponding to mentioned normal subjects. In some embodiments, the MRI device 220 can store the brain MRI, or transmit the brain MRI to specific storage devices. In some embodiments, alternative scanning devices for obtaining structures inside a brain can be used to replace the MRI device 220.

It is noted that the term "electrically coupling" or "communicatively coupling" can refer to physical or non-physical coupling. For example, in some embodiments, the processor 112 can be coupled the database 200 via physical cables. In some other embodiments, the processor 112 can be coupled to the MRI device 220 via some wireless communication standards. However, above embodiments are not intended to limit the fashion of unit coupling of the present disclosure. Vis such coupling, the processor 112 and the database 200 (or the MRI device 220) can establish unidirectional or bidirectional information exchanges.

Figure 2A:
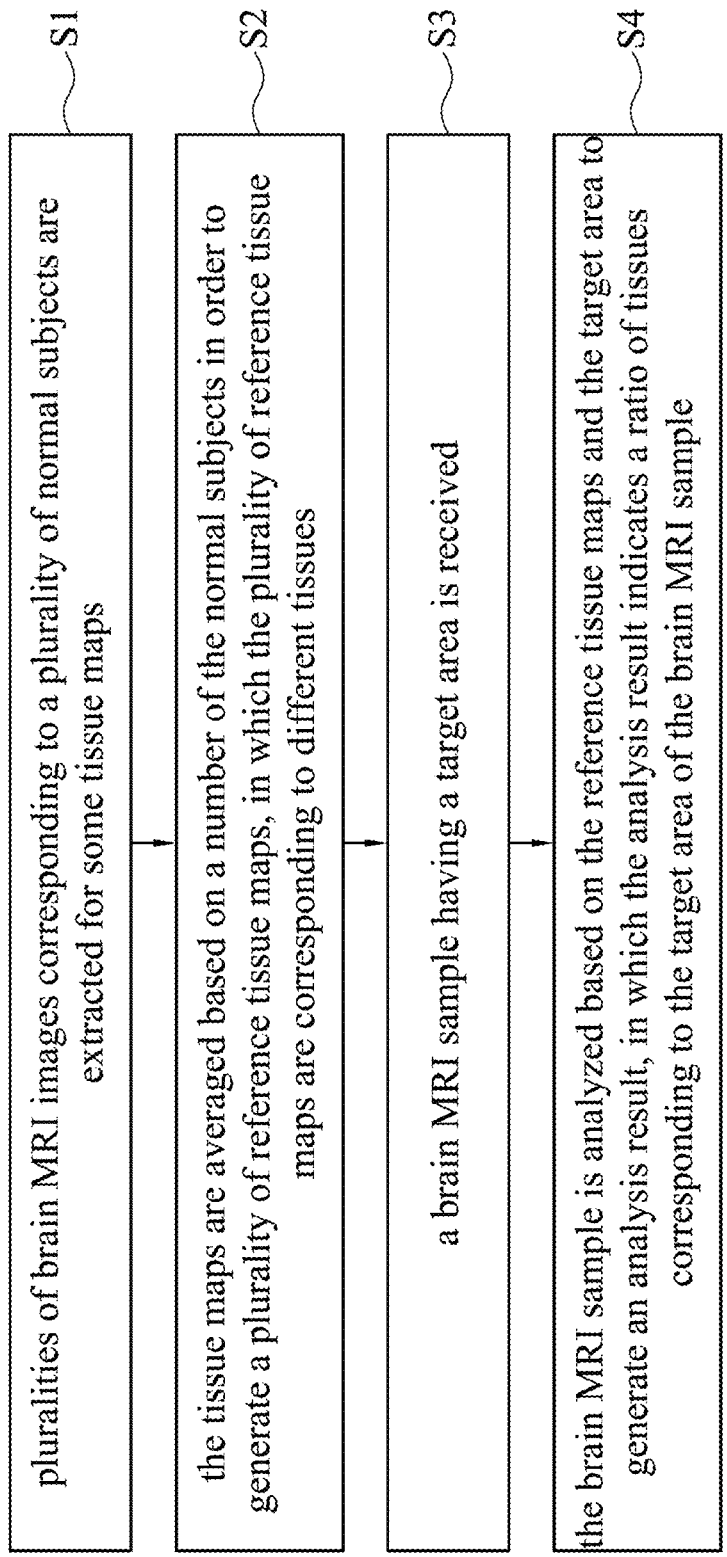
FIG. 2A is a flow chart showing a medical image analysis method according to some embodiments of the present disclosure.
Figure 2B:
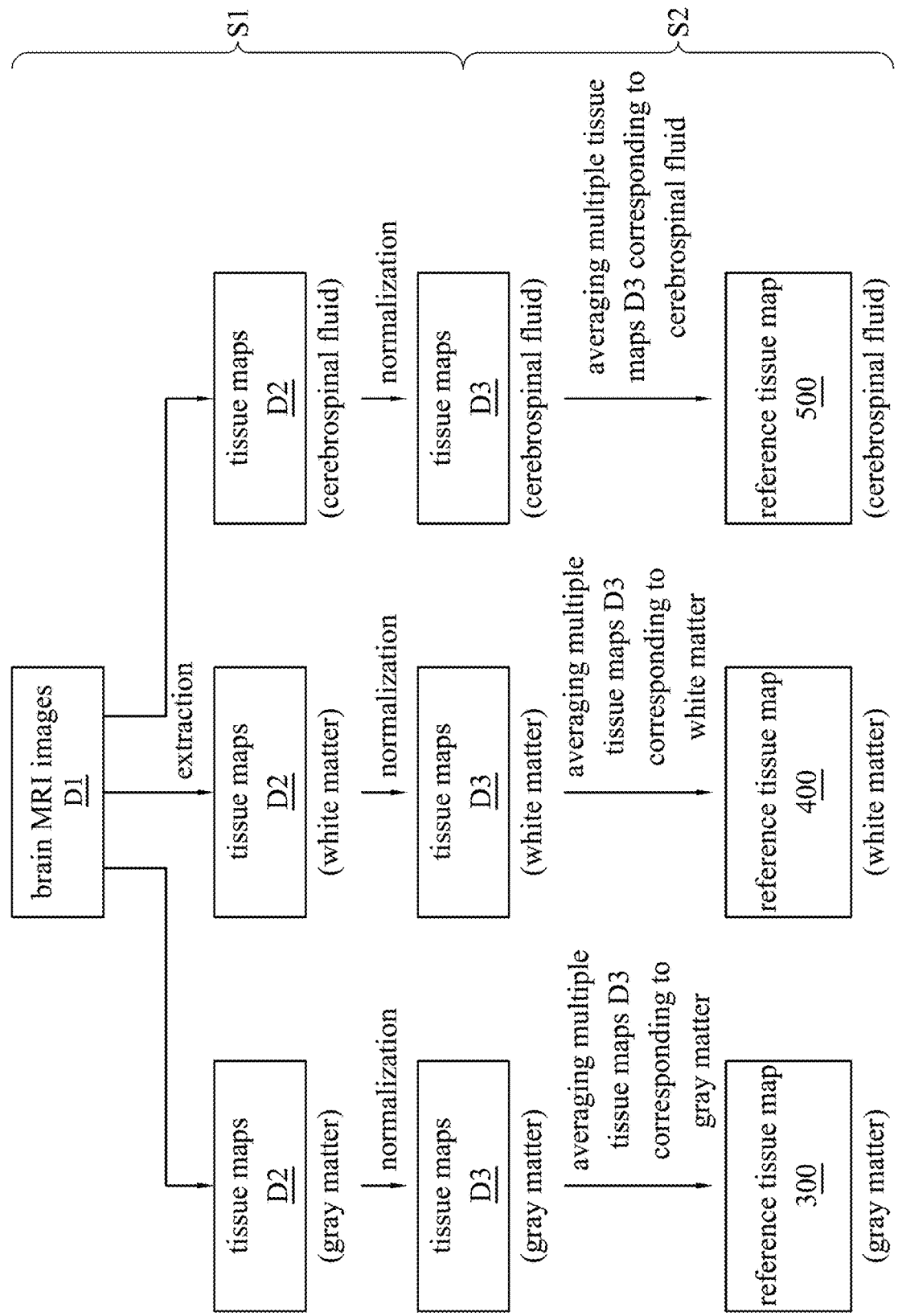
FIG. 2B is a flow chart showing some steps of the method of FIG. 2A according to some embodiments of the present disclosure.

FIG. 2A is a flow chart showing a medical image analysis method according to some embodiments of the present disclosure. As mentioned, the medical image analysis method can be a method for analyzing brain tissue based on magnetic resonance imaging. FIG. 2B is a flow chart showing the step S1 and the step S2 of the medical image analysis method of FIG. 2A according to some embodiments of the present disclosure. As shown in FIG. 2A, in some embodiments, the medical image analysis system 100 of FIG. 1 can be used to perform such medical image analysis method. In some embodiments, detail steps of the medical image analysis method are explained in following paragraphs.

Step S1: pluralities of brain MRI corresponding to a plurality of normal subjects are extracted for some tissue maps.

In some embodiments, the MRI device 220 can be used to scan brains of a specific number of normal subjects, in order to generate the brain MRID1 corresponding to the normal subjects. In some embodiments, the MRI device 220 can store the brain MRI D1. In some other embodiments, the MRI device 220 can transmit the brain MRI D1 to the database 200 so that the database 200 can store the brain MRI D1.

In some embodiments, the processor 112 can be selectively coupled to the database 200 or the MRI device 220. In this manner, the processor 112 can access the brain MRI D1 of the normal subjects from the database 200 or the MRI device 220.

In some embodiments, parameters for capturing of the brain MRID1 can be settled in the following: GE: MR750 3T; Coil: Head/Neck 8 channels; Sequence: 3D FSPGR; Plane: Axial; Repetition time (TR): 9.384 (ms); Echo time (TE): 4.036 (ms); Matrix: 256*92; Field of view (FOV): 256 mm*192 mm; Flip angle: 12°; Thickness: 1 mm. However, parameter settings of the present disclosure are not limited to this embodiment.

In some embodiments, the processor 112 can process the brain MRI D1 to extract a plurality of tissue maps D2. For instance, as shown in FIG. 2B, when the brain MRI D1 belongs to one normal subject is received, the processor 112 can execute an image analysis tool to process the brain MRI D1, in order to extract the tissue maps D2 corresponding to the gray matter, the white matter and the cerebrospinal fluid (CSF) respectively.

In some embodiments, a segment module of the statistical parametric mapping 12 (SPM 12) program can be used to implement mentioned image analysis tool.

In some embodiments, each of the tissue maps D2 corresponds to a specific tissue component of a human brain. For example, the tissue map D2 can at least include a gray matter map, a white matter map and a cerebrospinal fluid map. It is understood that the tissue maps can be considered a probability map indicating distributions of specific tissues in the entire brain. For instance, the gray matter map is a probability map indicating distributions of gray matters in the brain. As shown in a reference tissue map 300 of FIG. 3, a specific region with whiter color shows a higher probability (closer to 1) that this region contains gray matters. In opposite, a specific region with darker color shows a lower probability (closer to 0) that this region contains gray matters. The other maps can be read in the same way.

In some embodiments, the processor 112 can normalize the tissue map s D2 based on a diffeomorphic anatomical registration through exponential lie algebra (DARTEL), in order to map the tissue map s D2 to the standard brain space.

Since subjects can have different head shapes and/or head sizes, the normalize process can be introduced to the brain MRI of the normal subjects. In this manner, images with different head shapes and/or head sizes can be remapped to the same brain space. Following procedures can be benefit from such remapping. In some embodiments, the processor 112 can normalize multiple tissue maps D2 and store the normalized tissue maps D2 as tissue maps D3.

Step S2: the tissue maps are averaged based on a number of the normal subjects in order to generate a plurality of reference tissue maps, in which the plurality of reference tissue maps are corresponding to different tissues.

In some embodiments, the processor 112 can apply an average process to the tissue maps D3 based on a number of the subjects, in order to generate reference tissue maps 300, reference tissue maps 400 and reference tissue maps 500.

Figure 3:
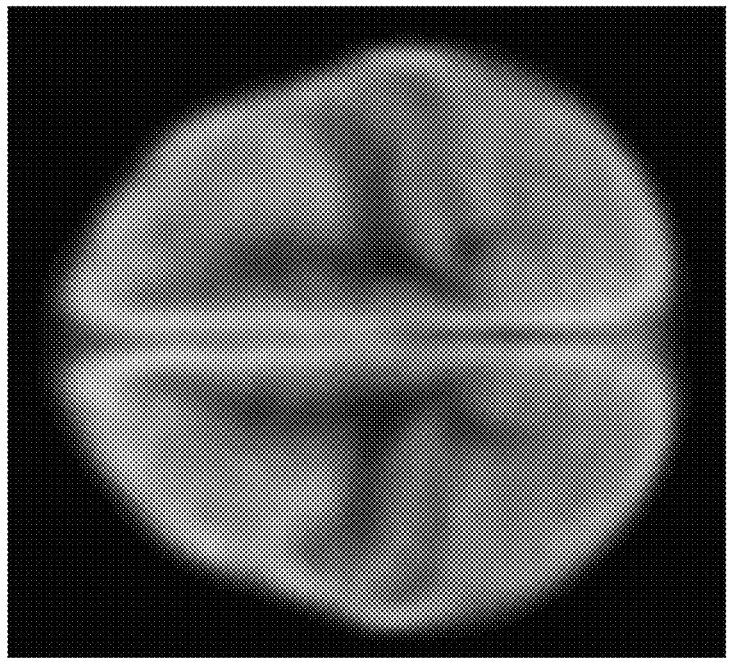
FIG. 3 is a schematic diagram showing a reference tissue map according to some embodiments of the present disclosure.

For example, as shown in FIG. 2B, when multiple tissue maps D3 corresponding to gray matter are collected, the processor 112 can average these tissue maps D3 of gray matters to output the reference tissue map 300 corresponding to gray matter (i.e. the one shown in FIG. 3). Similarly, the processor 112 can output the reference tissue map 400 corresponding to white matter (i.e. the one shown in FIG. 4) and the reference tissue map 500 corresponding to cerebrospinal fluid (i.e. the one shown in FIG. 5).

In some embodiments, the brain MRI D1 are collected from 22 normal subjects. These 22 normal subjects are at age 20-30. Mean of the subjects age is 25.3 and the standard deviation of the subjects age is 4.4. The processor 112 can sum up the distribution probabilities reflected by the gray matter maps extracted from the subjects brain MRI and has the probabilities divided by the subjects number (i.e. 22), in order to generate the reference tissue map corresponding to gray matters in the brain. Similarly, the processor 112 can obtain the reference tissue maps corresponding to gray matter, white matter, and cerebrospinal fluid, respectively. However, it is understood that the number of the subjects is not limited to this embodiment.

Figure 4:
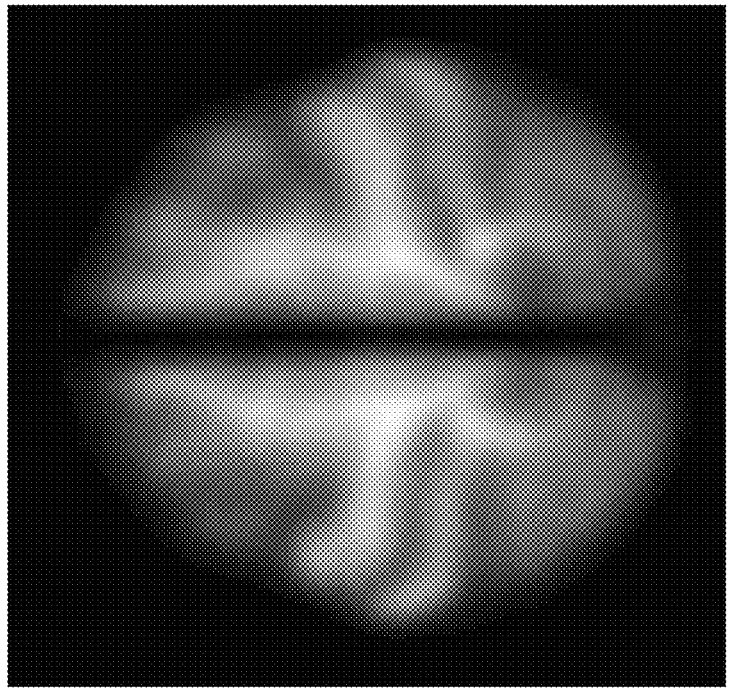
FIG. 4 is a schematic diagram showing a reference tissue map according to some embodiments of the present disclosure.
Figure 5:
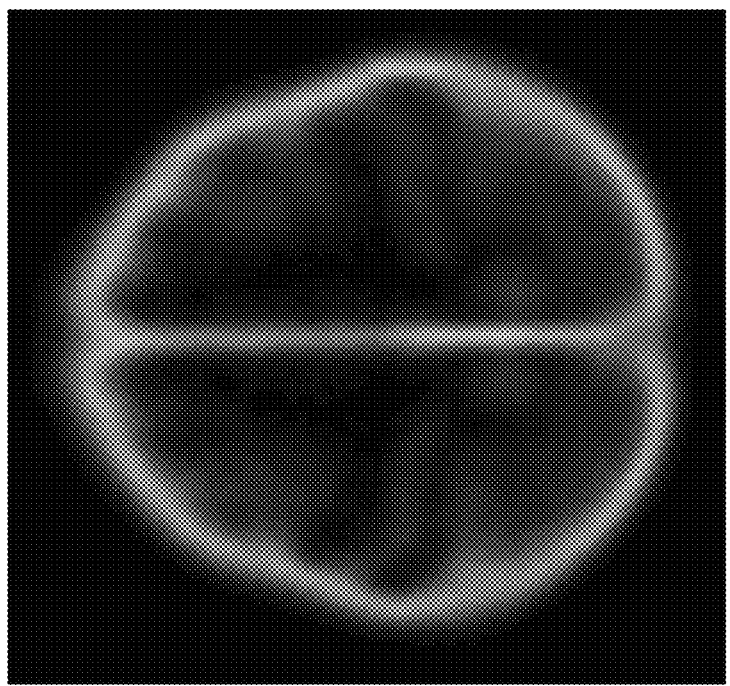
FIG. 5 is a schematic diagram showing a reference tissue map according to some embodiments of the present disclosure.

FIGS. 3-5 are schematic diagrams showing reference tissue maps 300, 400 and 500 according to some embodiments of the present disclosure. As mentioned, in some embodiments of FIG. 3, the processor 112 can generate a reference tissue map 300 of gray matter based on the brain MRI corresponding to said 22 normal subjects. In some embodiments, as shown in FIG. 4, the processor 112 can generate a reference tissue map 400 of white matter based on the brain MRI corresponding to said 22 normal subjects. In some embodiments, as shown in FIG. 5, the processor 112 can generate a reference tissue map 500 of cerebrospinal fluid based on the brain MRI corresponding to said 22 normal subjects. It is noted that, in some embodiments, according to the genders or the ages of subjects corresponding to the brain MRID1, the processor 112 can generate multiple reference tissue maps. Each of the reference tissue maps can be corresponding to subjects belongs to a specific gender or a specific age range.

It is noted that, in foregoing embodiments, the reference tissue maps corresponding to gray matter, white matter, and cerebrospinal fluid can be understood as being brain templates. These templates reflect average distribution of gray matters, white matters, and cerebrospinal fluids in the brains of the normal subjects.

Step S3: a brain MRI sample having a target area is received.

In some embodiments, the processor 112 can receive at least one brain MRI sample. It is noted that the brain MRI sample can be a scan result of a brain tumor patient.

Figure 6:
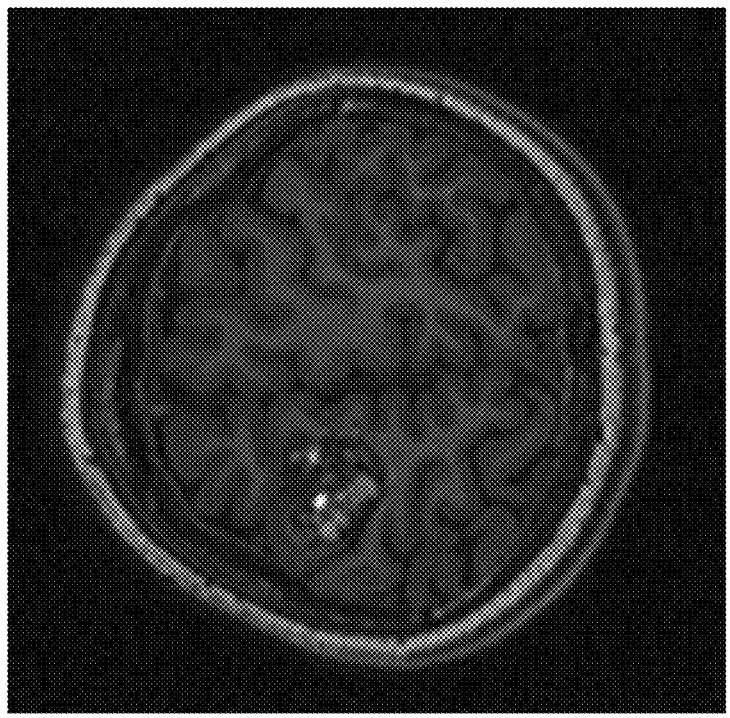
FIG. 6 is a schematic diagram showing a brain MRI sample according to some embodiments of the present disclosure.
Figure 7:
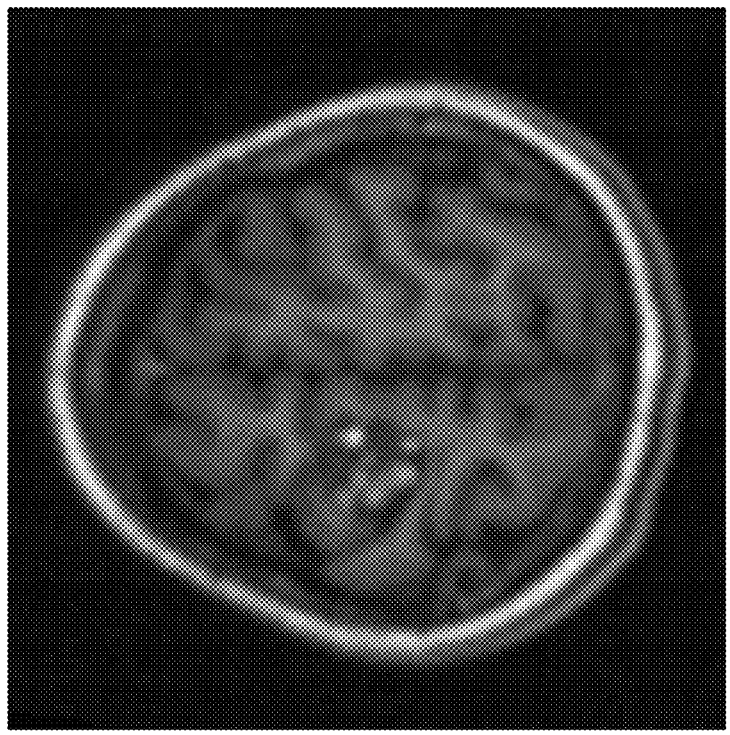
FIG. 7 is a schematic diagram showing a brain MRI sample according to some embodiments of the present disclosure.

FIG. 6 is a schematic diagram showing a brain MRI sample 600 according to some embodiments of the present disclosure. In some embodiments, the schematic diagram of FIG. 6 shows an original brain MRI sample belongs to a specific brain tumor patient. FIG. 7 is a schematic diagram showing a brain MRI sample according to some embodiments of the present disclosure. In some embodiments, the schematic diagram of FIG. 7 shows a normalized brain MRI sample 700 belongs to the specific brain tumor patient.

In some embodiments, the processor 112 can apply the diffeomorphic anatomical registration through exponential lie algebra to normalize the brain MRI sample 600 to generate the brain MRI sample 700. In some embodiments, the brain MRI sample 700 is remapped into the same standard brain space corresponding to the reference tissue map. In some embodiments, the brain MRI sample 600 can be obtained from a clinical case report.

In some embodiments, before the processor 112 receives the brain MRI sample 600, doctors or other diagnosis system can read the brain MRI sample 600 and mark a target area TA in the brain MRI sample 600. The target area TA can be a place that contains or possibly contains tumor tissues.

Figure 8:
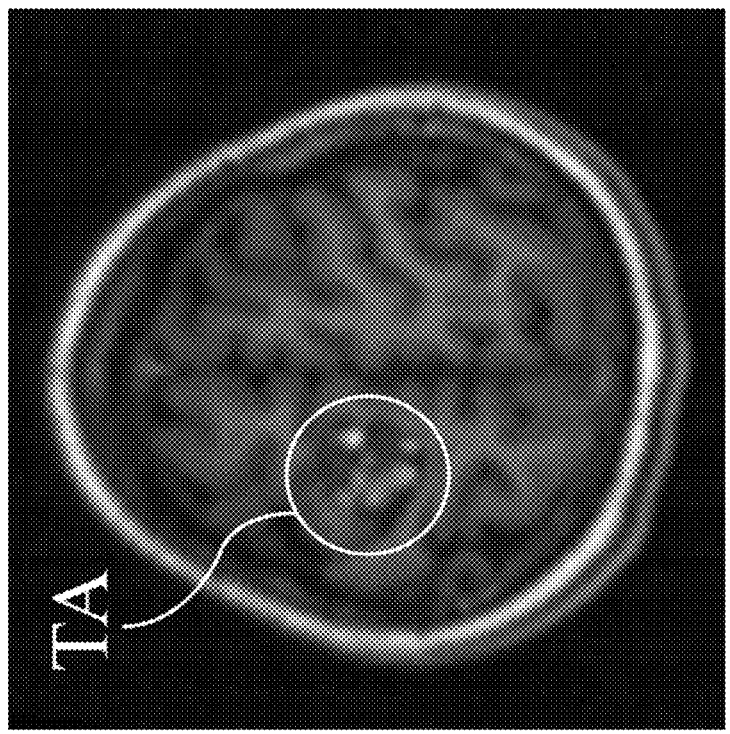
FIG. 8 is a schematic diagram showing a brain MRI sample according to some embodiments of the present disclosure.

FIG. 8 is a schematic diagram showing a brain MRI sample 800 according to some embodiments of the present disclosure. In some embodiments, the schematic diagram of FIG. 8 shows a normalized brain MRI sample 800 belongs to the specific brain tumor patient and the brain MRI sample 800 is marked with the target area TA. As shown in FIG. 8, the target area TA substantially corresponds to the tumor tissues in the brain. That is to say, the schematic diagram of FIG. 8 can be considered a result of the brain MRI sample 700 of FIG. 7 being marked with the target area TA.

Step S4: the brain MRI sample is analyzed based on the reference tissue maps and the target area to generate an analysis result, in which the analysis result indicates a ratio of tissues corresponding to the target area of the brain MRI sample.

In some embodiments, the processor 112 can compare the brain MRI sample 800 with the reference tissue map 300 corresponding to the gray matter, the reference tissue graph 400 corresponding to the white matter and the reference tissue map 500 corresponding to the cerebrospinal fluid, respectively, in order to generate an analysis result. The analysis result can indicate a ratio of tissues corresponding to the target area of the brain MRI sample. In some embodiments, since the brain MRI sample 800 is collected from a patent with a specific gender and a specific age, the processor 112 can compare the brain MRI sample 800 with the reference tissue maps obtained from normal subjects with the same gender and the same age.

More specifically, the analysis result can show a ratio of gray matter/white matter/cerebrospinal fluid in the target area, which is the percentages that the gray matter, the white matter and the cerebrospinal fluid relative to each other. For instance, since the reference tissue map 300, the reference tissue map 400, the reference tissue map 500 and the brain MRI sample 800 are already remapped into the standard brain space, where the target area TA located in the brain MRI sample 800 can be compared with the same spot in the reference tissue map 300-500. Hence, according to the reference tissue map 300, the processor 112 can obtain a gray matter ratio of 26.9% in the target area TA. According to the reference tissue map 400, the processor 112 can obtain a white matter ratio of 67.2% in the target area TA. According to the reference tissue map 500, the processor 112 can obtain a cerebrospinal fluid ratio of 5.3% in the target area TA.

As mentioned, brain tumor can trigger epilepsy syndromes, especially those spread to gray matters. Therefore, in some embodiments, the processor 112 can provide the analysis result for patients according to the above comparison process. The analysis result can show the ratio of gray matter/white matter/cerebrospinal fluid in the target area. Doctors can diagnose the spread of the tumor in gray matters according to the analysis result so the doctors can determine whether the patient can have epilepsy syndromes. In this way, the doctors can determine better therapeutic treatments for the patients.

In some embodiments, the analysis result can be used for research purposes. For example, researchers can input loads of brain MRI into the medical image analysis system 100 for training so that the processor 112 can obtain reference tissue maps with higher accuracies. Afterwards, researchers can input brain MRI samples belong to different patient into the processor 112 for analysis results. The analysis results can be sufficient for the researchers to obtain possible influences (e.g. brain functions or epilepsy syndromes) when tumors are located at different positions in the brain according to the brain MRI samples.

In some experiments used unrestricted conditions, a comparison between two ways for normal subjects' gray matter/white matter/cerebrospinal fluid ratio calculation are implemented. One is done by a system of prior art and another is done by the medical image analysis system 100 of the present disclosure. The comparison shows the average biases of the three tissues (gray matter, white matter, and cerebrospinal fluid) are 0.02%, −0.07% and 0.02%, respectively. These biases are considered marginal. The experiment proves a high accuracy of the medical image analysis system 100.

The shape of the target area TA in FIG. 8 is merely for exemplary purpose. In practice, different shapes of the target area TA can be possible. Though foregoing embodiments are provided with templates of brain tumor, gray matters, white matters and cerebrospinal fluids, the scope of the present disclosure is not limited thereto. Alternative applications can be covered by the scope of the present disclosure.

According to the foregoing embodiments, the present disclosure provides a medical image analysis system and method thereof. The system and the method can obtain a representative tissue map of a normal brain. The tissue map of the normal brain can be compared with a MRI sample of the patient to obtain accurate gray matter/white matter/cerebrospinal fluid components ratio effectively. In this way, the reliability of physician diagnosis and symptom researches can be increased.

Although various embodiments of the present disclosure are disclosed above, alternative implementations can be possible. Therefore, the scope of the present disclosure can be directed to the appended claims. Above embodiments are not intended to provide limitations to the present disclosure.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A system for analyzing brain tissue components based on magnetic resonance image, comprising:
   a memory, configured to store at least one instruction; and
   a processor, communicatively coupled to the memory, wherein the processor is configured to access and execute the at least one instruction to:
      extract a plurality of tissue maps from a plurality of brain magnetic resonance imaging (MRI) corresponding to a plurality of normal subjects, wherein the plurality of tissue maps are a plurality of probability maps indicating a plurality of probability distributions of a plurality of tissues in a brain, wherein the plurality of normal subjects are people different from a patient;
      sum up the plurality of probability distributions to divide by a number of the plurality of normal subjects, in order to generate a plurality of reference tissue maps, wherein the plurality of reference tissue maps are corresponding to different tissues;
      receive a brain MRI sample having a target area marked thereon; and
      analyze the brain MRI sample based on the plurality of reference tissue maps and the target area, in order to generate an analysis result, wherein the analysis result indicates a ratio of tissues corresponding to the target area of the brain MRI sample.

2. The system for analyzing brain tissue components based on magnetic resonance image of claim 1, wherein the plurality of tissue maps comprise a gray matter map, a white matter map and a cerebrospinal fluid map.

3. The system for analyzing brain tissue components based on magnetic resonance image of claim 2, wherein the ratio of tissues is a gray matter/white matter/cerebrospinal fluid ratio corresponding to the target area of the brain MRI sample.

4. The system for analyzing brain tissue components based on magnetic resonance image of claim 1, wherein the processor accesses and executes the at least one instruction to average the plurality of tissue maps comprising:
   normalize the plurality of tissue maps based on a diffeomorphic anatomical registration through exponential lie algebra, in order to map the plurality of tissue maps to a standard brain space; and
   average a plurality of first maps, which are corresponding to a first tissue from the plurality of tissues, from the plurality of normalized tissue maps, in order to generate a first reference tissue map of the plurality of reference tissue maps, wherein the first reference tissue map corresponds to the first tissue.

5. The system for analyzing brain tissue components based on magnetic resonance image of claim 1, wherein the target area is corresponding to a tumor position.

6. A method for analyzing brain tissue components based on magnetic resonance image, wherein the method is executed by a processor and comprises:
   extracting a plurality of tissue maps from a plurality of brain magnetic resonance imaging (MRI) corresponding to a plurality of normal subjects, wherein the plurality of tissue maps are a plurality of probability maps indicating a plurality of probability distributions of a plurality of tissues in a brain, wherein the plurality of normal subjects are people different from a patient;
   summing up the plurality of probability distributions to divide by a number of the plurality of normal subjects, in order to generate a plurality of reference tissue maps, wherein the plurality of reference tissue maps are corresponding to different tissues;
   receiving a brain MRI sample having a target area marked thereon; and
   analyzing the brain MRI sample based on the plurality of reference tissue maps and the target area, in order to generate an analysis result, wherein the analysis result indicates a ratio of tissues corresponding to the target area of the brain MRI sample.

7. The method for analyzing brain tissue components based on magnetic resonance image of claim 6, wherein the plurality of tissue maps comprise a gray matter map, a white matter map and a cerebrospinal fluid map.

8. The method for analyzing brain tissue components based on magnetic resonance image of claim 7, wherein the ratio of tissues is a gray matter/white matter/cerebrospinal fluid ratio corresponding to the target area of the brain MRI sample.

9. The method for analyzing brain tissue components based on magnetic resonance image of claim 6, wherein averaging the plurality of tissue maps comprising:
   normalizing the plurality of tissue maps based on a diffeomorphic anatomical registration through exponential lie algebra, in order to map the plurality of tissue maps to a standard brain space; and
   averaging a plurality of first maps, which are corresponding to a first tissue from the plurality of tissues, from the plurality of normalized tissue maps, in order to generate a first reference tissue map of the plurality of reference tissue maps, wherein the first reference tissue map corresponds to the first tissue.

10. The method for analyzing brain tissue components based on magnetic resonance image of claim 6, wherein the target area is corresponding to a tumor position.

* * * * *